(12) United States Patent
Reznik

(10) Patent No.: US 6,383,543 B1
(45) Date of Patent: May 7, 2002

(54) PROCESS FOR THE EXTRACTION OF AN ORGANIC SALT FROM PLANTS, THE SALT, AND OTHER SIMILAR SALTS

(75) Inventor: Rena Reznik, Ra'anana (IL)

(73) Assignee: RAD Natural Technologies Ltd., Petach Tikva (IL)

(*) Notice: Subject to any disclaimer, the term of this patent is extended or adjusted under 35 U.S.C. 154(b) by 0 days.

(21) Appl. No.: 09/869,065

(22) PCT Filed: Dec. 22, 1999

(86) PCT No.: PCT/IL99/00692

§ 371 Date: Jun. 21, 2001

§ 102(e) Date: Jun. 21, 2001

(87) PCT Pub. No.: WO00/39066

PCT Pub. Date: Jul. 6, 2000

(30) Foreign Application Priority Data

Dec. 24, 1998 (IL) ............................................. 127723
Feb. 18, 1999 (IL) ............................................. 128593

(51) Int. Cl.[7] ........................ A23L 1/223; A23L 1/221; A23L 1/22; C09K 15/08; C09K 15/34
(52) U.S. Cl. ..................... 426/431; 426/541; 426/542; 252/404; 252/398
(58) Field of Search ................................ 252/398, 404; 426/431, 541, 542, 654

(56) References Cited

U.S. PATENT DOCUMENTS

| | | | | | |
|---|---|---|---|---|---|
| 3,950,266 | A | * | 4/1976 | Chang et al. ............... | 252/398 |
| 4,012,531 | A | * | 3/1977 | Viani ........................ | 426/431 |
| 4,329,361 | A | * | 5/1982 | Zenk et al. ................. | 424/317 |
| 4,354,035 | A | * | 10/1982 | Christ et al. | |
| 4,450,097 | A | * | 5/1984 | Nakatani et al. ............ | 252/404 |
| 4,638,095 | A | * | 1/1987 | Chang et al. ............... | 568/326 |
| 4,857,325 | A | * | 8/1989 | Albeck et al. .............. | 424/195.1 |
| 4,877,635 | A | * | 10/1989 | Todd, Jr. ..................... | 426/542 |
| 4,923,697 | A | * | 5/1990 | Albeck et al. .............. | 424/195.1 |
| 4,986,985 | A | | 1/1991 | Grossman et al. .......... | 424/195.1 |
| 4,997,666 | A | * | 3/1991 | Albeck et al. .............. | 426/542 |

(List continued on next page.)

FOREIGN PATENT DOCUMENTS

| | | | |
|---|---|---|---|
| FR | 2652001 | 3/1991 | ............ A61K/7/42 |
| JP | 63162611 | 6/1988 | ............ A61K/7/00 |
| JP | 1121217 | 12/1989 | ......... A61K/31/215 |
| WO | WO9714319 | 4/1997 | ............ A23L/1/27 |
| WO | WO 97/14319 | * 4/1997 | |
| WO | WO9858656 | 12/1998 | .......... A61K/35/78 |
| WO | WO 98/58656 | * 12/1998 | |

OTHER PUBLICATIONS

Pryor et al., "A Rapid Screening Text to Determine the Antioxidant Potencies of Natural and Synthetic Antioxidants", J. Org. Chem., 58, 3521–3532 (1993).

Kelley, "The Polyphenolic Acids of LIthospermum Ruderale, II. Carbon–13 Nuclear Magnetic Resonance of Lithospermic and Rosmarinic Acids", J. Org. Chemistry, vol. 41, No. 3, (1976).

Primary Examiner—Joseph D. Anthony
(74) Attorney, Agent, or Firm—Abelman, Frayne & Schwab

(57) ABSTRACT

The invention relates to a completely water-soluble and long shelf-life antioxidant material comprising sodium rosmarinate, which has been extracted from tissue of plants of the Labiatae family without the necessity of adding extraneous sodium ions, and aqueous solutions comprising the antioxidant material, to sodium rosmarinate isolated from the extracted antioxidant material, to rosmarinic acid salts other than the sodium salt, or admixtures thereof with the sodium salt, obtained by cation-exchange with thus-isolated sodium rosmarinate, and to a process for preparing completely water-soluble antioxidant material comprising the sodium salt of rosmarinic acid, and its aqueous solutions.

10 Claims, 2 Drawing Sheets

U.S. PATENT DOCUMENTS

| | | | |
|---|---|---|---|
| 5,017,397 A | * 5/1991 | Nguyen et al. | 426/542 |
| 5,023,017 A | * 6/1991 | Todd, Jr. | 252/607 |
| 5,124,167 A | 6/1992 | Albeck et al. | 426/542 |
| 5,393,526 A | 2/1995 | Castro | 424/195.1 |
| 5,433,949 A | * 7/1995 | Kahleyss et al. | 424/195.1 |
| 5,908,650 A | * 6/1999 | Lenoble et al. | 426/262 |
| 6,306,450 B1 | * 10/2001 | Bank et al. | 426/534 |

* cited by examiner

PROCESS FOR THE EXTRACTION OF AN ORGANIC SALT FROM PLANTS, THE SALT, AND OTHER SIMILAR SALTS

FIELD OF THE INVENTION

The present invention relates to a material having antioxidant properties, and to a process for preparing such material.

BACKGROUND OF THE INVENTION

Artificial antioxidants such as butylated hydroxyanisole (BHA), butylated hydroxytoluene (BHT), tertiary-butylhydroxyquinone (TBHQ) and propyl gallate (PG) are known. However, in recent years, there has developed a movement towards avoiding using artificial additives, particularly where foodstuffs and medicaments are concerned. Much effort has therefore been invested in obtaining antioxidants from plants and especially from the Labiatae plant family.

Thus, in U.S. Pat. No. 3,950,266 (Chang et al.), there is described a process for extracting antioxidant material from rosemary or sage, using organic solvents boiling at up to 100° C. (examples of which are hexane, benzene, ethyl ether, chloroform, ethylene dichloride, dioxane and methanol) and subsequently carrying out various steps of purification. It appears that in all practical examples, before further purification, the crude antioxidant was washed with water, and then bleached with active carbon. It will be appreciated that antioxidant material produced in this manner will be solvent-soluble and water-insoluble.

By contrast, according to U.S. Pat. No. 4,012,531 (Viani), extraction of plant material is carried out in absence of organic solvents, under mildly alkaline conditions, using a basic aqueous buffer at pH from 7 to about 11.5, preferably in an inert atmosphere. Examples describe the extraction of rosemary, sage and parsley at pH 8.6–9.3, at 55–90° C.

In U.S. Pat. No. 4,450,097 (Nakatani et al.), antioxidant material is isolated from rosemary by extraction with a non-polar solvent, removal of the solvent and steam distillation, giving an aqueous dispersion, which was filtered, antioxidant being obtained from the solid material by further processing including extraction with aq. alkali at pH at least 10.5. An isolated antioxidant is 7β,11,12-trihydroxy-6,10-(epoxymethano)abieta-8,11,13-trien-20-one.

U.S. Pat. No. 4,638,095 (Chang et al.) describes the isolation from rosemary of the antioxidant "rosmaridiphenol", which is structurally a dibenzocycloheptene derivative. This compound was obtained by chromatographic separation (and appeared in the 75:25 diethyl ether/hexane fraction) of a product made by a procedure including solvent extraction and steam distillation.

U.S. Pat. No. 4,877,635 (Todd) describes a process for producing an oil-soluble extract of a Labiatae herb claimed to contain essentially all of the antioxidant substances in the herb, in the course of which acetone- or methyl ethyl ketone-insolubles, defined as pro-oxidant substances, are, so far as practicable, removed by precipitation. U.S. Pat. No. 5,023,017 (Todd) relates to a stable Labiatae antioxidant solution, having a pH 8.4–11.8, prepared from an initial solvent extract of the herb, and claimed to contain (besides<75% water, and an edible alcohol and/or polyol) essentially all of the antioxidant substances in the herb, which is preferably rosemary, sage or thyme.

U.S. Pat. No. 5,433,949 (Kahleyss et al.), after referring to U.S. Pat. No. 5,017,397 which describes preparation of antioxidants by extracting Labiatae species with $CO_2$ at 350–1000 bar and subsequent fractionation, proposes to prepare antioxidants from a similar source by a multistep process utilizing extraction with $CO_2$ at 80–300 bar, treating the extraction residue with a $C_{1-4}$ alcohol or $C_{5-7}$ hydrocarbon followed by active carbon, and washing out the resultant solvent extract with water to remove color, aromatics and remaining solvent.

It is evident that the various methods known to the prior art for obtaining antioxidants from plants of the Labiatae family have for the most part been based on the assumption that the desired materials are to be found in water-insoluble extracts obtained by extracting with non-aqueous solvents, particularly water-immiscible solvents, and in many of the relevant patents, aqueous fractions are rejected. Moreover, in Todd '635, acetone-insolubles are removed, being considered to contain undesired pro-oxidants, and in Todd '017 it is again emphasized that the acetone insoluble materials do not contain antioxidants. Although, as has been noted above, the Viani patent describes direct extraction of the plants with buffered aqueous alkali; the product on evaporation gives a mixture of the desired product with inorganic materials, separation from which entails at least a further step involving crystallization, ion-exchange treatment or acidification. Moreover, the present inventor has found that the product precipitated on acidification on Viani's alkaline solution is essentially water-insoluble.

In U.S. Pat. No. 4,354,035 (Christ et al.), there is described a process for isolating rosmarinic acid (of formula depicted below) from essentially water-immiscible organic solvent extracts of an aqueous extract made by extracting Melissa

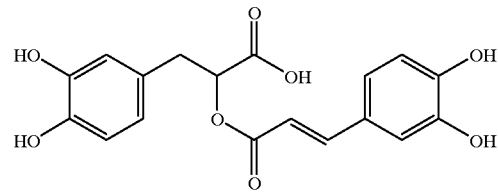

officinalis with water at 80–100° C., and acidifying to pH 2–2.5. This patent does not suggest that an industrially useful water-soluble product could be made directly from aqueous extracts of Melissa officinalis, without requiring use of water-immiscible organic solvent extracts.

According to the Christ et al. patent, rosmarinic acid is valuable in view of its antiinflammatory properties, see e.g. U.S. Pat. No. 4,329,361 (Zenk et al.). However, rosmarinic acid is also known for its use in skin-treatment or cosmetic compositions, see e.g. JP 63162611 and U.S. Pat. No. 5,393,526 (Castro). Moreover, rosmarinic acid is claimed to be useful in a composition for protection against erythema and inflammatory reactions caused by exposure to UV rays, and to have antioxidant, antibacterial and antifungal activity, see FR 2652001. The action of rosmarinic acid as a 5-lipoxygenase inhibitor is also featured in JP 1121217, where, extracted from perilla species, it is used as a constituent of an antiallergic food. Moreover, in FR 2652001, rosmarinic acid is used in a composition for protection against erythema and inflammatory reactions caused by exposure to UV rays, and is said to have antioxidant, antibacterial and antifungal activity. In FR 2652001, rosmarinic acid is extracted from powdered plants (after defatting and depigmenting by petroleum ether extraction) with 80% (aq.) alcohol and eluting with water on a cellulose column. Although Viani mentions rosmarinic acid, carnosic acid and pro-oxidant flavones, as extracted from rosemary at pH 8.5, there was no inference in this or other prior art, that the plants contained an extractable rosmarinic acid salt, or that this acid (or its derivatives) could per se be viable for antioxidant applications, i.e. to inhibit oxidation of other substances.

Mention is also made of the Albeck et al. and Grossman et al. patents (see U.S. Pat. Nos. 4,857,325, 4,923,697, 4,986,985, 4,997,666 and 5,124,167), which relate to the preparation of antioxidants by aqueous extraction of plant material specifying certain plant families and species, and utilization of such antioxidants. These patents neither disclose nor suggest that antioxidants might be obtained by similarly extracting plants of the Labiatae family, nor do they identify the chemical structure of the antioxidants.

The entire contents of the above-mentioned U.S. Patents are incorporated herein by reference.

Contrary to what is to be expected from the prior art, it has surprisingly been found by the present inventor that useful water-soluble and acetone-insoluble antioxidant material may be obtained from plants of the Labiatae family by extraction, which may be carried out at ambient temperatures, with aqueous extractant, by a process in which use of buffered alkali and a step of separation from admixed salts, need not arise.

It is thus an object of the present invention to provide a process for direct extraction of water-soluble antioxidant material from the plants in question, wherein plant material is extracted using weakly acidic, neutral or alkaline aqueous extractant.

It is a further object of the present invention to provide material which is highly efficient in terms of antioxidant activity, as compared with many known antioxidants used in industry.

Also, in view of much of the prior art on this subject, the inventor has unexpectedly found that conventionally rejected aqueous residues from the plant material in question, which has already been solvent extracted to remove water-insoluble solutes (including antioxidants such as carnosic acid), may nevertheless be used in the present process and afford in this manner useful antioxidant material. Thus, it is yet a further object of the present invention to provide a process for extraction of water-soluble antioxidant material from aqueous residues of known extraction processes wherein plants of the Labiatae family have already been subjected to extraction to remove water-insoluble solutes.

Another object of the invention is to provide a process permitting maximum recovery of industrially useful components from plants of the Labiatae family, including essential oils, completely water-soluble antioxidant material and known components which are both water-insoluble and organic solvent soluble, such as vitamin E and carnosic acid.

Yet another object of the invention is to provide a process for extraction of a water soluble antioxidant from natural plant materials which have had no contact with water-insoluble solvents and in which such solvents are not used in the extraction process and subsequently. Expressed in another way, it is regarded as an important object of the invention to provide such a process in which only plant materials and water, and optionally ethanol, are utilized to produce antioxidant material eminently suitable as an additive for human and animal consumption.

Other objects of the invention will become apparent from the description which follows.

SUMMARY OF THE INVENTION

It is believed that the present inventor is the first to recognize the presence of sodium rosmarinate in aqueous extracts from plant tissue of the Labiatae family and to isolate it therefrom. Accordingly, the present invention provides in one aspect, salts of the carboxylic function in rosmarinic acid, selected from a sodium salt isolated from tissue of plants of the Labiatae family, rosmarinic acid salts other than the sodium salt, or admixtures of said other salts with the sodium salt, which other salts or admixtures are those obtained by cation-exchange with said sodium salt from said tissue; an antioxidant material isolated by extraction from the tissue which is completely water-soluble and has a long shelf-life at ambient temperatures, and comprises the above-mentioned salt; and an aqueous solution which comprises such antioxidant material.

The antioxidant material of the invention, in powder form, has been found to have a shelf-life of at least two years at ambient temperatures.

A particular embodiment of the invention is constituted by a salt of the invention which has been chromatographically purified.

DETAILED DESCRIPTION OF THE INVENTION

Figure 1:
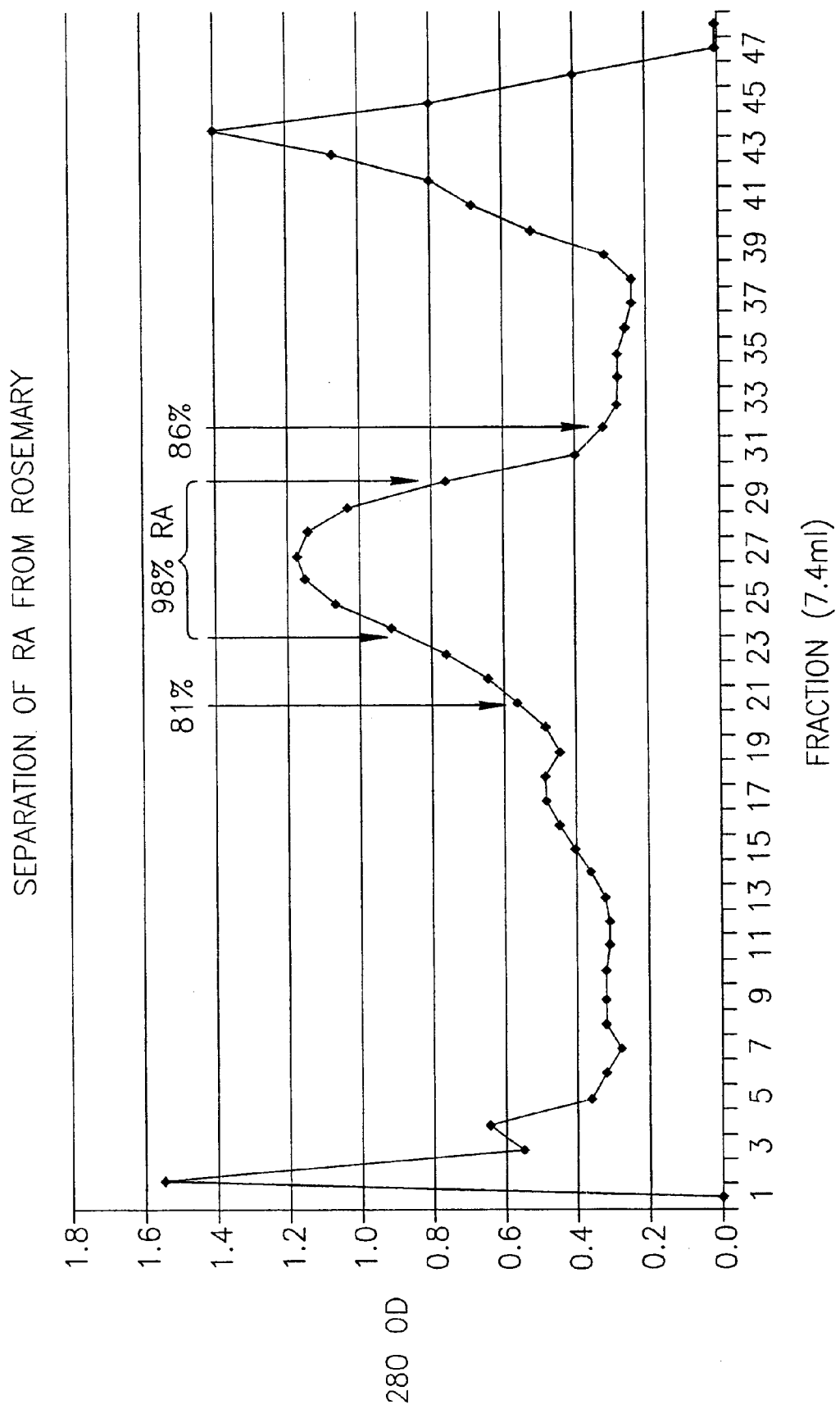
FIG. 1 illustrates chromatographic fractionation of antioxidant material from rosemary, in accordance with an embodiment of the invention.

The antioxidant material of the invention is at ambient temperatures completely soluble in water, as well as being insoluble in essentially 100% acetone and in hexane. The antioxidant material, the aqueous solution and the rosmarinic acid salts of the invention are obtained by processes which also constitute part of the present invention and which are detailed below.

Thus, in a particular embodiment, a process for the preparation of completely water-soluble antioxidant material comprising the sodium salt of rosmarinic acid, and of aqueous solutions containing as solute the antioxidant material, comprises effecting sequentially steps (a) and (b), followed by any one of steps (c), (d) and (e):

(a) subjecting tissue of plants of the Labiatae family to extraction with a first extractant selected from the group consisting of weakly acidic, neutral or alkaline aqueous extractants;

(b) separating the aqueous phase from insoluble matter; and either (c) extracting the separated aqueous phase, after concentration if desired, with a second extractant comprising aqueous ethanol, and separating the resultant aqueous organic phase which contains the antioxidant material; or (d) evaporating the separated aqueous phase to obtain the antioxidant material in solid form; or (e) subjecting the separated aqueous phase to chromatographic separation to recover a product enriched in the sodium salt of rosmarinic acid; provided that:

(α) where the extracted aqueous phase is alkaline, this is acidified and acid-insoluble material is removed prior to carrying out step (c), (d) or (e);

(β) where alkaline aqueous extractant is used, this contains as cations essentially only sodium ions.

In another embodiment, a process for the preparation of completely water-soluble antioxidant material comprising the at least one salt of rosmarinic acid, other than solely the sodium salt, and of aqueous solutions containing as solute the antioxidant material, comprises effecting sequentially steps (a) and (b), followed by any one of steps (c), (d) and (e):

(a) subjecting tissue of plants of the Labiatae family to extraction with a first extractant selected from the group consisting of alkaline aqueous extractants;

(b) separating the aqueous phase from insoluble matter, acidifying and removing acid-insoluble material; either (c) extracting the separated aqueous phase, after concentration if desired, with a second extractant comprising aqueous ethanol, and separating the resultant aqueous organic phase which contains the antioxidant material or (d) evaporating the separated aqueous phase to obtain the antioxidant material in solid form; or (e) subjecting the separated aqueous phase to chromatographic separation to recover a product enriched in the at least one salt of rosmarinic acid; provided that the cations in the alkaline aqueous extractant are selected according the cations desired in the product and are not exclusively sodium ions. The cations may be selected from e.g. sodium, lithium, potassium, ammonium and substituted ammonium cations.

In the embodiment just described, cation exchange between sodium ions of the naturally occurring sodium rosmarinate and other cations is effected as part of the preparative process. It will be apparent to persons of the art, however, that salts other than the sodium salt could also be obtained by chemically equivalent methods, such as first isolating the sodium salt (as a solid or in solution) and subsequently running a solution of the sodium salt through an ion-exchange column containing desired other cations.

Optional features of the process of the invention include the following:

(i) the plants are selected from oregano, rosemary, sage and thyme;

(ii) the first extractant is a non-buffered alkaline aqueous extractant;

(iii) where the process comprises consecutive steps (a), (b) and (c), then the separated aqueous phase is concentrated by evaporation to remove the major part of the water present prior to extraction with the second extractant;

(iv) where the process which comprises consecutive steps (a), (b) and (c), then the second extractant is ethanol containing a minor amount of water;

(v) where the process comprises consecutive steps (a), (b) and (c), then it includes the additional step of evaporating the separated organic phase from step (c), thereby to obtain the antioxidant material in solid form;

(vi) the solid antioxidant material obtained in step (d) or from the additional step is subjected to a further step of chromatographic purification;

(vii) prior to step (a) the tissue has been subjected to at least one of the following preliminary operations, namely: drying, comminuting, steam distillation or extraction with water-immiscible organic solvents to recover water-insoluble constituents;

(viii) separated insoluble matter from step (b) is subjected to extraction with water-immiscible organic solvents to recover water-insoluble constituents.

In yet another embodiment, a process for the recovery of useful constituents from tissue of plants of the Labiatae family, comprises subjecting the tissue to the sequential steps of steam distillation to recover essential oils, recovery of completely water-soluble antioxidant material according to the process of the invention set forth above, and further extraction of the separated aqueous-extracted insoluble matter from step (b) with at least one water-immiscible organic solvent, to recover water-insoluble and organic solvent soluble constituents, such as vitamin E and carnosic acid, but which in any case have been to a great extent documented in the literature. It will be apparent that optional features (i) to (vi), above, may be applied also to this process embodiment.

The tissue to be subjected to extraction with aqueous extractant in accordance with the invention may be Labiatae plant tissue and in particular the preferably (but not necessarily) dried superficial growing parts of the plants, i.e. stems, leaves and flowers. The tissue may be in a fine state of subdivision, which can be achieved by milling or homogenization of the tissue, and it may be convenient to carry out the extraction in accordance with the invention in the same vessel as homogenization. However, it has surprisingly been found in accordance with a presently preferred embodiment of the invention, that if the plant tissue is first subjected to the action of steam to distil off essential oils, this action simultaneously apparently opens the pores in the tissue with the effect that, without any grinding, maceration or comminution, and even without mixing, merely allowing the residual tissue from steam distillation to stand with water for a readily ascertainable relatively brief time period, is adequate to allow viable extraction of water soluble antioxidant material in accordance with the invention.

Without prejudice to the generality of the invention, the plant tissue extracted may be e.g. from oregano, rosemary, sage or thyme.

As mentioned above, step (a) of the process of the invention may be carried out in weakly acidic, neutral or alkaline solution, but it is presently preferred to carry out the extraction in an essentially neutral medium, or in other words, without the addition of weakly acidic or alkaline substances which may entail subsequently, additional separation steps and thus detract from the overall economy of the process. In contrast to the process described in the Viani patent (above), the present process is not concerned with the essentially water-insoluble material which is precipitated when a buffered alkaline extract is acidified.

Step (a) may be carried out at between ambient temperatures and about 100° C.

In the process comprising steps (a), (b) and (c), the second extractant referred to above is preferably ethanol containing a minor amount of water, and in any event, whatever the identity of the second extractant, the separated aqueous phase is preferably concentrated by evaporation to remove the major part of the water present prior to extraction with the second extractant.

Moreover, in a particular embodiment of the process comprising steps (a), (b) and (c), there may be included an additional step of evaporating the separated organic phase from step (c), thereby to obtain the completely water soluble antioxidant material in solid form. This solid, or the solid obtained in step (d), may be subjected to the further step of chromatographic purification, in a manner generally known to persons of the art, but which in a presently preferred embodiment is described in further detail below.

The evaporation step referred to herein may be carried out by any suitable method known to persons of the art, e.g. by lyophilization or spray drying, and the obtained residue may be used as such. Alternatively, the residue may be extracted with aqueous ethanol, and the extract is concentrated and dried e.g. by lyophilization or spray drying. As is shown in the Examples below, the lyophilized extracted concentrate thus obtained may have a relatively high antioxidant activity and efficiency, even though HPLC analysis shows that antioxidant activity may constitute only about 50% of the product at this stage. However, further purification of the product to attain a higher degree of purity may be achieved by chromatographic means, whereby a product having high antioxidant activity and a dramatically improved antioxidant efficiency may be obtained.

The invention will be illustrated by the following non-limiting examples.

EXAMPLE 1

Aqueous Extraction of Raw Rosemary Plant Tissue (a) A mixture of the dried superficial growing parts of rosemary plants (i.e. stems, leaves and flowers), 2 g, was homogenized with 10 ml water and maintained at ambient temperature (about 24° C.) for one hour. The pH of the mixture during this extraction was about 6.5. The supernatant was separated from residual plant tissue and lyophilized to give 0.2 g (10% yield) of a crude completely water-soluble product containing about 10% antioxidant-active substance, the activity of crude product being 430 units/mg.

(b) When the extraction in (a) was repeated, except that citric acid was added initially to give pH 2, it was found that the supernatant had a pH of about 7 and that the crude completely water-soluble lyophilized product had approximately the same antioxidant activity as before.

(c) When the extraction in (a) was repeated, except that NaOH was added initially to give pH 11, it was found that the resultant supernatant had a pH of about 7 and that the crude completely water-soluble lyophilized product had approximately the same antioxidant activity as before.

(d) When the extraction in (a) was repeated, except that the rosemary plant tissue had been treated with steam and extracted with ether, prior to aqueous extraction, it was found that the crude completely water-soluble lyophilized product had approximately the same antioxidant activity as before.

(e) (comparative example) Rosemary plant tissue (5 g) was vigorously stirred with 50 ml $Na_2CO_3/NaHCO_3$ buffer at pH 8.6 and 90° C., essentially as described in Example 2 of U.S. Pat. No. 4,012,531 (Viani). Extraction of a portion of the reaction mixture with aqueous acetone and lyophilization of the product (after evaporation of the acetone), at this stage, gave a product containing only 5% of the antioxidant material of the present invention (as identified by a sharp peak on HPLC separation and elution with aqueous methanol at between 14 and 15 minutes retention time), thus showing that the desired product remained dissolved in the alkaline medium. A separate portion of the reaction mixture was then acidified as suggested by Viani and as carried out by Todd (see Example 2 of U.S. Pat. No. 5,023,017), both Viani and Todd utilizing only the precipitate as "antioxidant". The precipitate was filtered off and was found to be almost completely water-insoluble. The filtrate, after concentration, extraction with aqueous acetone and lyophilization of the product (after evaporation of the acetone) gave a completely water-soluble antioxidant material, 28% pure in the desired product, according to HPLC. This experiment demonstrates inter alia that Viani's aqueous alkaline extract did not contain a completely water-soluble solute.

(f) Rosemary or oregano plant tissue was first subjected to the action of steam at 100° C. for about one hour to recover essential oils by steam distillation. Water was added to the residue and the mixture was allowed to stand at 60–100° C. for about 2–45 minutes, filtered and the filtrate containing about 4% solute was concentrated to about 40% solute, again filtered and spray-dried. The yellowish powder product contained about 9.5% antioxidant active substance and could be used as such or was subject to chromatographic purification. It was found that while a relatively long work-up time resulted in a darker-colored product (light brown to brown), the high antioxidant activity of the product (about 430 units/mg) was independent of its color. Yield of the powder was as follows:

| Run | Extraction conditions | Yield from 25 g plant tissue |
|---|---|---|
| 1 | 20 minutes at 80° C. | 0.7 g (2.8%) |
| 2 | 45 minutes at 80° C. | 1.2 g (4.8%) |
| 3 | 20 minutes at 100° C. | 1.2 g (4.8%) |
| 4 | 45 minutes at 100° C. | 1.4 g (5.6%) |
| 5 | run 4 residue extracted with 125 ml water for 15 minutes at 100° C. | +0.4 g (+1.6%) |
| 6 | run 5 residue extracted with 125 ml water for 15 minutes at 100° C. | +0.28 g (+1.1%) |
| 4–6 | (combined) | 2.08 g (8.3%) |

Example 1 shows inter alia that the prior art practice of obtaining antioxidant material from Labiatae family plants, from organic solvent soluble extracts, while rejecting aq. fractions, and/or rejecting acetone-insolubles, results in substantial loss of potentially valuable antioxidant. Moreover, Example 1(c) shows surprisingly, that contrary to Viani and Todd, useful completely water-soluble antioxidant material can be obtained by alkaline extraction.

EXAMPLE 2

Method for Determination of Antioxidant Activity

The method is based on the rate of oxidation of linoleic acid (LA) to its conjugated diene hydroperoxide (Pryor et al., in J. Org. Chem., 1993, 58 (13): 3521–3532), and 2,2'-azobis (2-amidinopropane).2HCl (ABAP) is used to provide a constant rate of radical production. A 1% LA aq. emulsion was prepared with 1% Tween 20 and 0.05M sodium phosphate buffer (pH 7.4). A control sample contained 0.025 ml of the LA emulsion+2.87 ml. of the buffer+ 0.1 ml 0.05M ABAP; a test sample contained 0.05 ml of the LA emulsion+2.7–2.8 ml of the buffer+0.1 ml 0.05M ABAP+0.05–0.1 ml of the sample under test. Absorption at 234 nm is followed for 5 minutes to establish the uninhibited rate of autoxidation. The test antioxidant in a concentration of 1 mg/ml is then checked to get 50% inhibition, which defines one unit (e.g., if 20 µl inhibits 50%, this is one unit and thus the antioxidant activity is 1000/20=50 units/mg). The test antioxidant was added and the inhibited reaction was followed until the antioxidant was consumed and the rate of the absorption change at 234 nm reverted to that observed at the outset.

EXAMPLE 3

Chromatographic Purification and Identification of Antioxidant

A column of 8 cm×1 cm is packed with MacroPrep-methyl (hydrophobic interaction 40 µm, Bio-Rad) was washed exhaustively with water and ethanol, and then used for purification of the water extract lyophilizate (see Example 1(f), above). 200 mg of the lyophilizate was dissolved in 1 ml water, and the solution was loaded on the MacroPrep column that had been pre-equilibrated with water. Elution was carried out using a 0.1% acetic acid/70:30 ethanol in water gradient starting with a 100:0 ratio at 0 minutes and ending with a 0:100 ratio at 220 minutes, and at a flow rate of 2.0 ml/minute. Peaks are monitored by UV absorption at 280 nm. The column effluent was collected after 85 minutes (193 ml) and the active material was found to be eluted between 85 to 100 minutes (36 ml, 30–40% ethanol (balance water).

Figure 2:
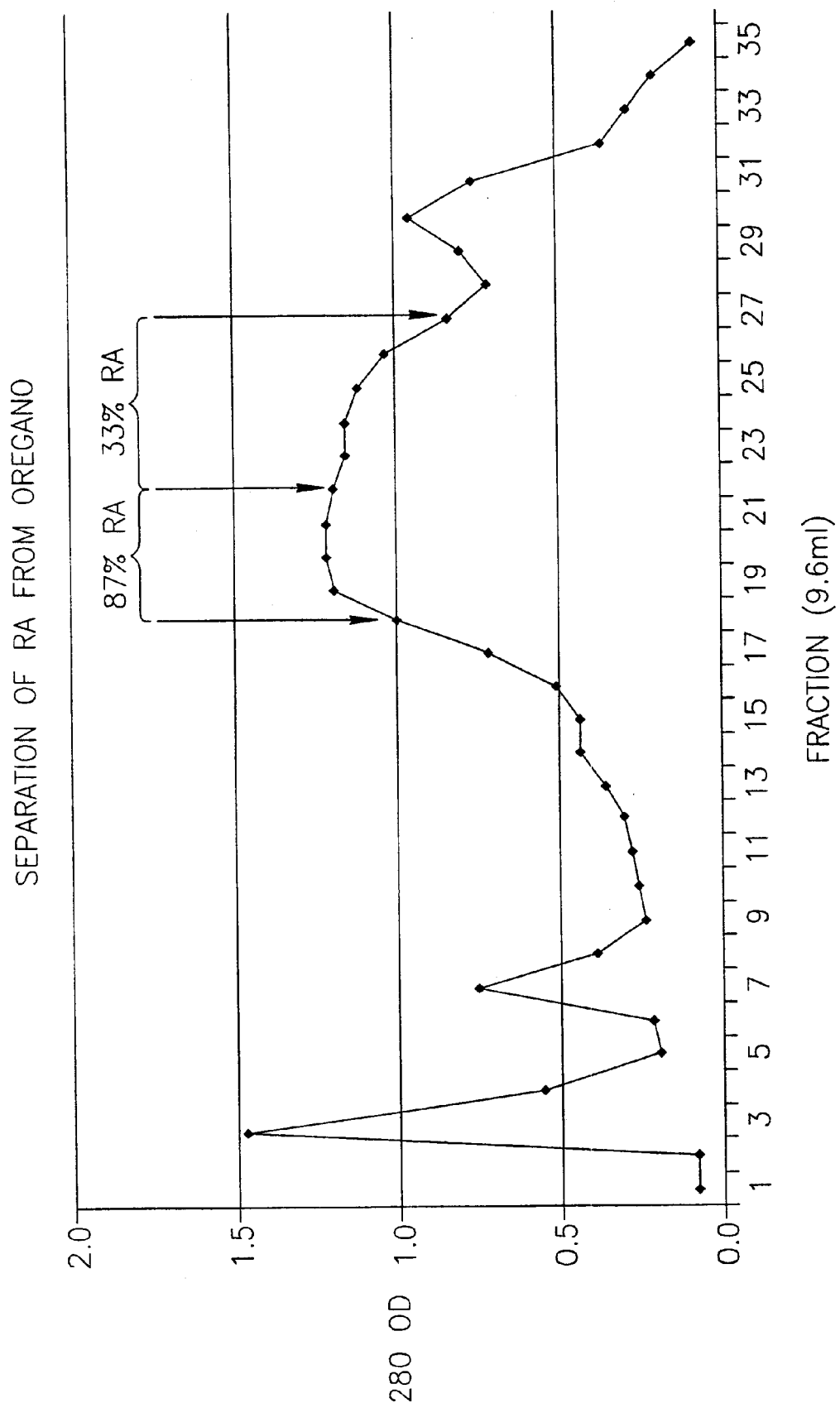
FIG. 2 illustrates chromatographic fractionation of antioxidant material from oregano, in accordance with an embodiment of the invention.

The progressive increase in purity of the above operations was determined by HPLC on RP-18, using a water/methanol gradient starting with a 100:0 ratio at 0 minutes and ending with a 30:70 ratio at 15 minutes, and at a flow rate of 1 ml/minute. Results are shown, together with other relevant purification data, in FIGS. 1 and 2 (where "RA" denotes rosmarinic acid, sodium salt) and in the following table, where "% purity" means % in the product in question, of antioxidant material identified by a sharp peak on HPLC separation and elution with aqueous methanol at between 10.68–10.72 mins. retention time:

| Fraction | Amount crude antioxidant (mg) | % Purity | Rosmarinate (mg) | Yield (%) |
|---|---|---|---|---|
| rosemary extract (FIG. 1) | 200 | 10 | 20 | 100 |
| 21–23 | 4 | 81 | 3.2 | 16 |
| 24–30 | 15 | 98 | 14.7 | 7.35 |
| 31–32 | 2 | 86 | 1.6 | 8.4 |
|  |  |  | total = | 97.7 |
| oregano extract (FIG. 2) | 200 | 10 | 20 | 100 |
| 18–22 | 18 | 87 | 15 | 75 |
| 23–27 | 15 | 33 | 4.6 | 23 |
|  |  |  | total = | 98.0 |

Both $^1$H and $^{13}$C NMR spectra were measured for the chromatographically pure antioxidant of the invention. It was found that there were only very small shift differences in the chemical shift values for a $d_6$-DMSO solution, compared with corresponding data reported for rosmarinic acid ($d_6$-acetone for $^1$H and $D_2O$ for $^{13}$C) see Kelley, C. J. et al., J. Org. Chem. 40: 1804 (1975) and ibid., 41: 449 (1976). These differences, taken together with the fact rosmarinic acid is acetone-soluble and the present compound is virtually acetone-insoluble, are consistent with identification of the present product as a carboxylate salt of rosmarinic acid. The compound was identified as sodium rosmarinate, and the formula weight (282) for $C_{18}H_{15}NaO_8$ was confirmed by mass spectra.

EXAMPLE 4

Stability and Comparative Efficiency of Antioxidants (a) Stability

The lyophilizate obtained from the aqueous extract has a shelf-life with substantially unchanged antioxidant activity of more than two years at 24° C. This lyophilizate (6 mg) was dissolved in 0.5 g glycerol, and 0.25 g of the solution was placed in a tube which was then incubated at 180° C. for 15 minutes. A second similar tube was used as a control at room temperature. Following incubation, 1.5 ml water was added to each tube and the activity was checked. There was found to be no change in the activity in the control and in the tube incubated at 180° C. Moreover, an aqueous extract of rosemary at pH 4 could be kept at ambient temperature for at least 12 months, with retention of antioxidant activity.

(b) Comparative efficiency

Ex. 2 is followed, but it is carried out until antioxidant is consumed and the rate of change of absorption at 234 nm had reverted to that observed at the control. Efficiency is calculated as the time 1 mg of antioxidant continues to inhibit oxidation of linoleic acid. Results are shown in the following table.

| Antioxidant | Efficiency of 10 μg (hrs) | Solubility | Toxicity |
|---|---|---|---|
| (prior art:) |  |  |  |
| Vitamin E | 444 | lipid | no |
| Vitamin C | 93 | water | no |
| BHT | 814 | lipid | yes |
| Trolox* | 650 | water | no |
| PG | 500 | lipid | yes |
| TBHQ | 432 | lipid | yes |
| Rosemary oil | 201 | lipid | no |
| present invention |  |  |  |
| 98% pure | 1413 | water | no |

*water-solubilized vitamin E

It may be concluded from the foregoing results that the antioxidant of the invention is considerably more efficient than the known antioxidants against which it has been tested. This is true even of the lyophilizate obtained from the aqueous extract as described above and the efficiency of the product is seen to rise dramatically on further purification.

EXAMPLE 5

Antioxidant Effect in Emulsions Containing Soybean Oil (a) Oil in water emulsions were prepared from soybean oil (10%), Tween 80 (7%), Span 80 (3%), water (80%) and antioxidant (0.1 or 0.02%). Antioxidant performance at 50° C. as measured by the TBA (thiobarbituric acid) test were as follows:

| Antioxidant | Concentration (%) | Days until oxidation |
|---|---|---|
| BHA | 0.02 | 2 |
| Vitamin E | 0.1 | 1 |
| Vitamin C | 0.1 | 1 |
| Rosemary Extract* | 0.02 | 4 |
| Rosemary Extract* | 0.1 | 4 |

*see below (b) Water in oil emulsions from soybean oil (85%), PGPR emulsifier (Croda, 5%), water (10%) and antioxidant (0.1 or 0.02%) gave test results at 100° C., as measured by the Rancimat (AOM) test, as follows:

| Antioxidant | Concentration (%) | Hours until oxidation |
|---|---|---|
| BHA | 0.02 | 9.54 |
| Vitamin E | 0.1 | 9.58 |
| Vitamin C | 0.1 | 25.20 |
| Rosemary Extract* | 0.02 | 19.05 |
| Rosemary Extract* | 0.1 | 29.00 |

*water-soluble, containing 10% sodium rosmarinate; the concentration of the latter in the emulsions is thus, respectively, 0.002 and 0.01

EXAMPLE 6

Antioxidant Effect in Bulk Oil

A concentrate was first prepared containing 40% lecithin, 40% oil (e.g. soybean oil), 20% propylene glycol and 4% based on the foregoing mixture of 65% (≡2.6% pure) sodium rosmarinate. Rosmarinic acid can alternatively be substituted for the sodium salt.

The thus-prepared concentrate can then be used in a bulk oil which it is desired to protect against oxidative deterioration. Where the oil is soybean oil, test results at 60° C. were as follows:

| Antioxidant | Concentration | Days until oxidation |
|---|---|---|
| (prior art:) | | |
| None | | 4 |
| Vitamin E | 0.06% | 4 |
| BHA | 0.02% | 4 |
| Rosemary oil | 0.4% | 6 |
| present invention | | |
| sodium rosmarinate | 0.005%¤ | 7 |
| sodium rosmarinate | 0.013%♦ | 8 |

¤ as 0.2% of the above concentrate
♦ as 0.5% of the above concentrate

EXAMPLE 7

Antioxidant Effect in Emulsions Containing β-Carotene

β-Carotene (6 mg), linoleic acid (1 ml) and Tween 40 (2 ml) were dissolved in chloroform, the mixture was concentrated in a rotary evaporator, and the last traces of chloroform were removed by nitrogen. A model emulsion was then prepared by adding double-distilled water (25 ml) to the residue and diluting to 500 ml with phosphate buffer (pH 7.0). A solution (2 ml) of the inventive antioxidant was mixed with 50 ml aliquots of the emulsion, such that antioxidant concentration was 0.005, 0.01 or 0.02%. Comparison samples contained BHA in concentrations of 0.01 and 0.02%, and ascorbic acid (0.1%). A control sample contained no antioxidant but instead, 95% ethanol (2 ml). It was found that over a 100 hour time period, the inventive antioxidant afforded a similar order of protection to β-carotene as did BHA, whereas little protection was afforded by ascorbic acid.

EXAMPLE 8

Stabilization of Ascorbic Acid

It is known that ascorbic acid is subject to oxidative deterioration, and in particular that its aqueous solutions are rapidly oxidized by air. For the purpose of this example, ascorbic acid was dissolved in 50% ethanol, and the solution, in a closed bottle, was placed in an oven at 60° C. for 24. hours. The experiment was repeated with the addition of 0.035 mg or 0.07 mg sodium rosmarinate. Each sample was diluted 1:10 and the ascorbic acid content was analyzed by HPLC on a 250 cm×4 mm RP-18 column, and eluting with 30:70 acetonitrile water at a flow rate of 1 ml/min. The peak area absorption at 245 nm, compared with the initial area, corresponded with the amount of ascorbic acid in each case, the results being as follows:

| Sample (10 mg/ml ascorbic acid) | HPLC peak area (245 nm) | % ascorbic acid |
|---|---|---|
| control | 12,334,252 | 100 |
| after 60° C., 24 hours (no additive) | 5,572,750 | 45 |
| after 60° C., 24 hours (+0.035 mg rosmarinic acid*) | 8,384,409 | 68 |
| after 60° C., 24 hours (+0.07 mg rosmarinic acid*) | 11,130,666 | 90 |

*Na salt

These results show that rosmarinic acid (and its derivatives) effectively protects ascorbic acid from decomposition under the given conditions, particularly at the higher concentration of 0.7%. It may be inferred that the extent of this protection would be considerably greater under other conditions, e.g. at ambient temperatures and or when the ascorbic acid is not necessarily in the form of an aqueous solution.

EXAMPLE 9

Inhibition of Oxidation of Essential Oils (a) Orange Essential Oil

Different concentrations of romarinate solution were added to 5 ml orange essential oil. The samples were kept at 30° C. for seven days, and were then checked for peroxide using the TBA test. The rosmarinate solution ("Organox os") contained 17% propylene glycol, 65% lecithin and 17% sodium rosmarinate (50% pure). Additionally, oxidation at 4° C. without antioxidant was noted for comparison. The results were as follows:

| Essential oil | % Organox os | % rosmarinate | oxidation (TBA) |
|---|---|---|---|
| 5 ml, 30° C. | 0 | 0 | 0.525 nm |
| 5 ml, 30° C. | 0.1 | 0.008 | 0.445 nm |
| 5 ml, 30° C. | 0.2 | 0.017 | 0.370 nm |
| 5 ml, 30° C. | 0.25 | 0.021 | 0.340 nm |
| 5 ml, 30° C. | 0.3 | 0.025 | 0.310 nm |
| 5 ml, 4° C. | 0 | 0 | 0.320 nm |

(b) Grapefruit Oil

This test was carried out similarly to part (a), above, except that the samples were kept for eleven days. The results were as follows:

| Essential oil | % Organox os | % rosmarinate | oxidation (TBA) |
|---|---|---|---|
| 5 ml, 30° C. | 0 | 0 | 0.150nm |
| 5 ml, 30° C. | 0.1 | 0.008 | 0.105nm |
| 5 ml, 30° C. | 0.2 | 0.017 | 0.080nm |
| 5 ml, 4° C. | 0 | 0 | 0.080nm |

(c) Orange Oil (colorless)

This test was carried out similarly to part (a), above, except that the samples were kept for eleven days. The results were as follows:

| Essential oil | % Organox os | % rosmarinate | oxidation (TBA) |
|---|---|---|---|
| 5 ml, 30° C. | 0 | 0 | 1.8 nm |
| 5 ml, 30° C. | 0.1 | 0.008 | 1.3 nm |
| 5 ml, 30° C. | 0.155 | 0.013 | 1.0 nm |
| 5 ml, 30° C. | 0.2 | 0.017 | 0.9 nm |
| 5 ml, 30° C. | 0.25 | 0.021 | 0.65 nm |
| 5 ml, 4° C. | 0 | 0 | 0.70 nm |

Conclusions

By using a relatively small amount of antioxidant at 30° C., it is possible to achieve approximately the same level of inhibition of oxidation, in essential oils, for the given period, compared with refrigeration at 4° C.

While the present invention has been particularly described with reference to certain embodiments, it will be apparent to those skilled in the art that many modifications and variations may be made. The invention is accordingly not to be construed as limited in any way by such embodiments, rather its concept is to be understood according to the spirit and scope of the claims which follow.

What is claimed is:

1. Process for the preparation of completely water-soluble antioxidant material comprising the sodium salt of rosmarinic acid, and of aqueous solutions containing as solute said antioxidant material, which process comprises effecting sequentially steps (a) and (b), followed by any one of steps (c), (d) and (e):

(a) subjecting tissue of plants of the Labiatae family to extraction with a first extractant selected from the group consisting of weakly acidic, neutral and alkaline aqueous extractants at temperature $\leq 80°$ C.;

(b) separating the aqueous phase from insoluble matter; and either (c) extracting said separated aqueous phase, after concentration if desired, with a second extractant comprising aqueous ethanol, and separating the resultant aqueous organic phase which contains said antioxidant material; or (d) evaporating said separated aqueous phase to obtain said antioxidant material in solid form; or (e) subjecting said separated aqueous phase to chromatographic separation to recover a product enriched in said sodium salt of rosmarinic acid; provided that:

($\alpha$) where said extracted aqueous phase is alkaline, this is acidified and acid-insoluble material is removed prior to carrying out step (c), (d) or (e);

($\beta$) where alkaline aqueous extractant is used, this contains as cations essentially only sodium ions.

2. Process according to claim 1, wherein at least one of the following conditions is satisfied:

(i) said plants are selected from the group consisting of oregano, rosemary, sage and thyme;

(ii) said first extractant is a non-buffered alkaline aqueous extractant;

(iii) where said process comprises consecutive steps (a), (b) and (c), then said separated aqueous phase is concentrated by evaporation to remove the major part of the water present prior to extraction with said second extractant;

(iv) where said process comprises consecutive steps (a), (b) and (c), then said second extractant is ethanol containing a minor amount of water;

(v) where said process comprises consecutive steps (a), (b) and (c), then said process includes the additional step of evaporating said separated organic phase from step (c), thereby to obtain said antioxidant material in solid form;

(vi) said solid antioxidant material obtained in step (d) is subjected to a further step of chromatographic purification;

(vii) prior to step (a) said tissue has been subjected to at least one of the following preliminary operations, namely: drying, comminuting, steam distillation or extraction with water-immiscible organic solvents to recover water-insoluble constituents;

(viii) separated insoluble matter from step (b) is subjected to extraction with water-immiscible organic solvents to recover water-insoluble constituents.

3. Process for the recovery of useful constituents from tissue of plants of the Labiatae family, which comprises subjecting said tissue to the sequential steps of steam distillation to recover essential oils, recovery of completely water-soluble antioxidant material according to the process of claim 1, and further extraction of the separated aqueous-extracted insoluble matter from step (b) with at least one water-immiscible organic solvent, to recover water-insoluble and organic solvent soluble constituents.

4. Process according to claim 3, wherein at least one of the following conditions is satisfied:

(i) said plants are selected from selected from the group consisting of oregano, rosemary, sage and thyme;

(ii) said first extractant is a non-buffered alkaline aqueous extractant;

(iii) where said process comprises consecutive steps (a), (b) and (c), then said separated aqueous phase is concentrated by evaporation to remove the major part of the water present prior to extraction with said second extractant;

(iv) where said process which comprises consecutive steps (a), (b) and (c), then said second extractant is ethanol containing a minor amount of water;

(v) where said process comprises consecutive steps (a), (b) and (c), then said process includes the additional step of evaporating said separated organic phase from step (c), thereby to obtain said antioxidant material in solid form;

(vi) said solid antioxidant material obtained in step (d) is subjected to a further step of chromatographic purification.

5. Process for the preparation of completely water-soluble antioxidant material comprising the at least one salt of rosmarinic acid, other than solely the sodium salt, and of aqueous solutions containing as solute said antioxidant material, which process comprises effecting sequentially steps (a) and (b), followed by any one of steps (c), (d) and (e):

(a) subjecting tissue of plants of the Labiatee family to extraction with a first extractant selected from the group consisting of alkaline aqueous extractants;

(b) separating the aqueous phase from insoluble matter, acidifying and removing acid-insoluble material; and either (c) extracting said separated aqueous phase, after concentration if desired, with a second extractant comprising aqueous ethanol, and separating the resultant aqueous organic phase which contains said antioxidant material; or (d) evaporating said separated aqueous phase to obtain said antioxidant material in solid form; or (e) subjecting said separated aqueous phase to chromatographic separation to recover a product enriched in said at least one salt of rosmarinic acid; provided that the cations in said alkaline aqueous extractant are selected according the cations desired in the product and are not exclusively sodium ions.

6. Process according to claim 5, wherein at least one of the following conditions is satisfied:

(i) said plants are selected from the group consisting of oregano, rosemary, sage and thyme;

(ii) said first extractant is a non-buffered alkaline aqueous extractant;

(iii) where said process comprises consecutive steps (a), (b) and (c), then said separated aqueous phase is concentrated by evaporation to remove the major part of the water present prior to extraction with said second extractant;

(iv) where said process comprises consecutive steps (a), (b) and (c), then said second extractant is ethanol containing a minor amount of water;

(v) where said process comprises consecutive steps (a), (b) and (c), then said process includes the additional step of evaporating said separated organic phase from step (c), thereby to obtain said antioxidant material in solid form;

(vi) said solid antioxidant material obtained in step (d) is subjected to a further step of chromatographic purification;

(vii) prior to step (a) said tissue has been subjected to at least one of the following preliminary operations, namely: drying, comminuting, steam distillation or extraction with water-immiscible organic solvents to recover water-insoluble constituents;

(viii) separated insoluble matter from step (b) is subjected to extraction with water-immiscible organic solvents to recover water-insoluble constituents.

7. Process for the recovery of useful constituents from tissue of plants of the Labiatae family, which comprises subjecting said tissue to the sequential steps of steam distillation to recover essential oils, recovery of completely water-soluble antioxidant material according to the process of claim 5, and further extraction of the separated aqueous-extracted insoluble matter from step (b) with at least one water-immiscible organic solvent, to recover water-insoluble and organic solvent soluble constituents.

8. Process according to claim 5, wherein the cations in said alkaline aqueous extractant are selected from sodium, lithium, potassium, ammonium and substituted ammonium cations, but are not exclusively sodium cations.

9. Process according to claim 8, wherein at least one of the following conditions is satisfied:

(i) said plants are selected from selected from the group consisting of oregano, rosemary, sage and thyme;

(ii) said first extractant is a non-buffered alkaline aqueous extractant;

(iii) where said process comprises consecutive steps (a), (b) and (c), then said separated aqueous phase is concentrated by evaporation to remove the major part of the water present prior to extraction with said second extractant;

(iv) where said process comprises consecutive steps (a), (b) and (c), then said second extractant is ethanol containing a minor amount of water;

(v) where said process comprises consecutive steps (a), (b) and (c), then said process includes the additional step of evaporating said separated organic phase from step (c), thereby to obtain said antioxidant material in solid form;

(vi) said solid antioxidant material obtained in step (d) is subjected to a further step of chromatographic purification;

(vii) prior to step (a) said tissue has been subjected to at least one of the following preliminary operations, namely: drying, comminuting, steam distillation or extraction with water-immiscible organic solvents to recover water-insoluble constituents;

(viii) separated insoluble matter from step (b) is subjected to extraction with water-immiscible organic solvents to recover water-insoluble constituents.

10. Process for the recovery of useful constituents from tissue of plants of the Labiatae family, which comprises subjecting said tissue to the sequential steps of steam distillation to recover essential oils, recovery of completely water-soluble antioxidant material according to the process of claim 8, and further extraction of the separated aqueous-extracted insoluble matter from step (b) with at least one water-immiscible organic solvent, to recover water-insoluble and organic solvent soluble constituents.

* * * * *